United States Patent
Manalis et al.

[11] Patent Number: 6,002,131
[45] Date of Patent: Dec. 14, 1999

[54] SCANNING PROBE POTENTIOMETER

[75] Inventors: Scott R. Manalis, Santa Barbara, Calif.; Stephen C. Minne, Danville, Ill.; Calvin F. Quate, Stanford, Calif.

[73] Assignee: The Board of Trustees of the Leland Stanford Junior University, Palo Alto, Calif.

[21] Appl. No.: 09/047,887

[22] Filed: Mar. 25, 1998

[51] Int. Cl.⁶ .................................................. G01R 29/12
[52] U.S. Cl. ......................... 250/306; 324/458; 324/690
[58] Field of Search ............................... 250/306, 315.3; 324/458, 690

[56] References Cited

U.S. PATENT DOCUMENTS

| | | | |
|---|---|---|---|
| 4,969,978 | 11/1990 | Tomita et al. | 250/306 |
| 4,985,627 | 1/1991 | Gutierrez et al. | 250/306 |
| 5,065,103 | 11/1991 | Slinkman et al. | 250/306 |

OTHER PUBLICATIONS

Stern, J., et al., Deposition and imaging of localized charge on insulator surfaces using a force microscope, Appl. Phys. Lett., 53, p. 2717, 1988.

Terris, B., et al., Contact Electrification Using Force Microscopy, Am. Phys. Soc., 63(24), pp. 2669–2672, 1989.

*Primary Examiner*—Jack I. Berman
*Attorney, Agent, or Firm*—Lumen Intellectual Property Services

[57] ABSTRACT

A system for scanning and measuring a surface charge of a sample immersed in a conductive medium, such as an aqueous electrolytic solution or a gel, or positioned on a conducting plate. The system has a semiconductor with a probing surface clad in a charge-sensitive layer. The probing surface moves over the sample during scanning while a bias voltage $V_{BIAS}$ is applied to create a depletion layer in the semiconductor and to induce the system to alter a measurable electrical property. The electrical property is monitored with the aid of a measuring device and the measurement is correlated to the sample's surface charge. In a preferred embodiment the semiconductor is a part of a cantilever structure of the type having a probing tip and the probing surface is located on the apex of the probing tip thereby enabling examination of the topology and surface charge of the sample concurrently.

25 Claims, 8 Drawing Sheets

SCANNING PROBE POTENTIOMETER

GOVERNMENT INTEREST

This invention was developed with government support under a grant from ONR JSEP contract no. N00014-91-J-1050. The government has certain rights in the invention.

FIELD OF THE INVENTION

This invention relates to an apparatus and a method of measuring the charge distribution over a surface using a scanning probe potentiometer (SPP).

BACKGROUND OF THE INVENTION

The light-addressable potentiometric sensor (LAPS) is a device developed to potentiometrically measure changes in pH, redox potential and transmembrane potential in a highly sensitive manner (see Hafeman et al., Science, Vol. 240, 1182 (1988)). The LAPS consists of an insulated semiconductor device which is immersed in an electrolyte. The sample of interest is placed on the surface of the insulator (at the insulator-electrolyte interface) and a bias voltage is generated such that the solution is negative with respect to the semiconductor. The insulator consists of a pH-sensitive material, such as silicon nitride or silicon oxinitride, or other charge-sensitive material. Electron-hole pairs are created in the semiconductor by a pulsed intensity-modulated light source, resulting in separation of charges in an area called the depletion region of the semiconductor. The electrons in the depletion region migrate, thereby causing a current of a magnitude that depends on the bias voltage and the chemistry of the sample at the adjacent insulator-solution interface. This movement of electrons yields a detectable alternating current in the external circuit.

An alternative measurement approach is based on the fact that the width of the depletion layer is related to the surface potential. The width of the depletion layer can be determined by measuring the capacitance between the semiconductor and the electrolyte.

A useful feature of using light excitation, is that different regions of the device may be monitored by selectively irradiating the location of interest, thereby allowing multiple potentiometric measurements with the use of multiple LEDs. The resultant photocurrent is monitored, giving a real-time measurement of, for instance, pH changes. Such measurements typically yield an RMS noise of 0.0005 to 0.001 pH units in a 1 Hz bandwidth. The primary utility of LAPS has been in commercial microphysiometers to measure the rate of proton excretion from cells by measuring the pH of a nearby surface (see McConnell et al., Science, Vol. 257, 1906 (1992)). The existing art in the field of LAPS provides for monitoring cell metabolism in terms of overall pH changes, redox potentials, and quantitative determinations of analytes for bulk samples. These systems, however, are not suitable for uses such as mapping charge distribution over very small areas or detecting chemical dynamics on the molecular level with high spatial resolution.

In the field of surface inspection several techniques have been developed for detecting charge on a surface. These methods exploit features of the general technique of scanning probe microscopy (SPM). One variant of SPM is based on an atomic force microscope (AFM) designed to map surface charge (for details about AFM see, e.g., Binning et al., Phys. Rev. Lett., Vol. 56, 930 (1986). Briefly, in traditional AFM a tip is mounted on a cantilever with a small spring constant and scanned over a surface such that the repulsive interatomic forces between the surface and the tip cause deflections in the cantilever. A feedback system is used to monitor and control the force between the tip and sample, and optical detection techniques such as interferometry or laser beam deflection are used to measure the resultant cantilever deflection during scanning.

An adaptation of AFM for SPM to map a charge distribution on a sample surface is discussed by B. D. Terris et al. in "Contact Electrification Using Force Microscopy", Physical Review Letters, Vol. 63, No. 24, pp. 2669–72 (1989). The charge measurement is based on the fact that the presence of charge on the scanned surface alters the spring constant of the cantilever. In the absence of any surface charge the typical spring constant is on the order of 0.2 N/m and the resonant frequency around 25 kHz. When the tip of the cantilever approaches a charge the tip-to-surface force gradient changes due to the Coulomb field. This change affects the cantilever's spring constant and consequently its resonant frequency. For efficient charge measurement an AC bias is applied between the tip and a back electrode to produce an oscillating charge on the tip. This enables one to measure surface charge via variations in the cantilevers oscillation response. For additional information refer to J. E. Stern et al., "Deposition and Imaging of Localized Charge on Insulator Surfaces Using a Force Microscope", Applied Physics Letters, Vol. 53, pp. 2717 (1988).

Improvements to SPM instrumentation have allowed for increased sensitivity and speed; however, there is no existing SPM that successfully scans a surface and measures its electrical properties in such a way that the measured signal is unaffected by incongruent tip-sample force interactions from topographic features. Additionally, the existing techniques do not allow one to measure charge with high sensitivity by scanning a sample while immersed in a fluid or gel.

OBJECTS AND ADVANTAGES OF THE INVENTION

In light of the prior art and its limitations, the present invention provides a system and method of measuring charge on a surface using a scanning probe potentiometer (SPP). The SPP provides a new use of the concept of LAPS such that miniaturization and selectability are enhanced significantly.

Accordingly, it is a primary object of the present invention to provide a method and apparatus for measuring the charge and potential of a surface. Specifically, the method and apparatus are intended to allow measurements on sample surfaces immersed in fluids or gels, or measuring the surface potential of samples without the presence of a fluid or gel.

It is a further object to provide a method and apparatus for spatially mapping the adsorption of charged molecules on a surface.

It is another object to provide a method and apparatus for measuring the charge and potential of a surface with a lateral resolution of well below 0.1 microns. Additionally, the method and apparatus provide for scanning to measure the charge and potential over surface areas as large as 1 $mm^2$ and more.

These and other objects and advantages will become apparent from the following description and accompanying figures.

SUMMARY OF THE INVENTION

The objects and advantages of the invention are achieved by a system for scanning and measuring a surface charge of a sample. The sample may be immersed in a conductive medium, such as an aqueous electrolytic solution or a gel, or positioned on a conducting plate. The system has a semiconductor with a probing surface which moves over the sample during scanning. The scanning can involve a simple point-contact or a raster-type scan of the entire sample of the surface and it is performed by a scanning mechanism which produces relative movement between the probing surface and the sample.

A charge-sensitive layer is disposed on the probing surface. An electrical arrangement is provided for creating a bias voltage $V_{BIAS}$ between the medium in which the sample is immersed or the conducting plate on which the sample is positioned and the semiconductor. The application of the bias voltage $V_{BIAS}$ creates a depletion layer in the semiconductor below the charge-sensitive layer. Under these conditions the system responds to the charge distributed on the sample by altering an electrical property. The electrical property is monitored with the aid of a measuring device and the measurement is correlated to the sample's surface charge.

For example, the electrical property is an AC current produced in the semiconductor in response to an amplitude modulated light beam and the device for measuring this electrical property is an ammeter. The amplitude of the AC current is related to the width of the depletion layer which, in turn, is related to surface potential or charge on the surface of the charge-sensitive layer. Alternatively, the electrical property is a capacitance between the semiconductor and the medium or the conducting plate. In this case the device for measuring this electrical property is a capacitance sensor.

It is preferable to include the semiconductor in a cantilever structure of the type having a probing tip. The probing surface is located on the probing tip and covered with the charge-sensitive layer. Any deflection system can be used to detect the deflection experienced by the cantilever during sample scan. Most preferably, however, the laser deflection system is a laser based arrangement generating a light beam at an amplitude modulated frequency e tuned to penetrate into the semiconductor and create electron-hole pairs in the semiconductor that give rise to the AC current (photocurrent) when they are split apart in the depletion region. This optimizes the design and allows for examining the topology and measuring the surface charge of the sample concurrently.

The system of the invention accommodates various types of samples. For example, the sample can include materials such as DNA, RNA, proteins, receptors, antibodies, bacteria, viruses, polymers, cells, organelles, membranes and the like.

The method of the invention teaches scanning of the sample to determine its surface charge. Preferably, the method is employed in conjunction with a topological scan.

The apparatus and the method of the invention are described in detail in the below description with reference to the attached drawing figures.

DETAILED DESCRIPTION

Figure 1:
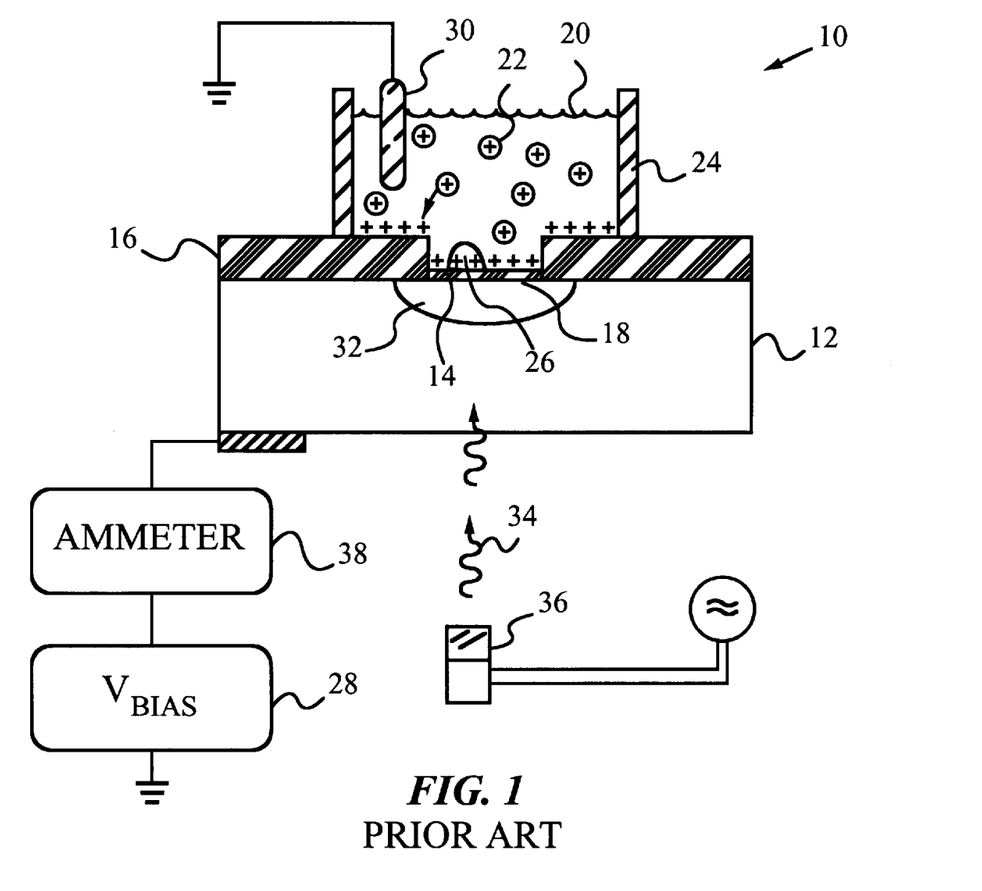
FIG. 1 is a cross sectional view of a prior art Light-Addressable Potentiometric Sensor (LAPS).

To appreciate how the apparatus and method of the invention differ from the prior art it is instructive to review a well-known Light-Addressable Potentiometric Sensor or LAPS 10 which is shown in FIG. 1. LAPS 10 has a semiconducting substrate 12 such as a silicon plate with a probing surface 14 on which is deposited a charge-sensitive layer 16; typically a surface insulator of silicon oxinitrile. Charge sensitive layer 16 has a thin region 18 where measurements on a sample 26 are performed. In fact, sample 26 is immersed in an ion 22 containing aqueous electrolyte 20 kept in a container 24 above charge sensitive-layer 16.

To operate LAPS 10 a bias voltage $V_{BIAS}$ is applied between semiconductor 12 and the surface of layer 16 in region 18 using a voltage generator 28 and an electrode 30. Thus, region 18 with sample 26 is maintained at $V_{BIAS}$ with respect to semiconductor 12 and this produces a depletion layer 32 in semiconductor 12 next to probing surface 14. In this state semiconductor 12 generates an alternating current in response to illumination with intensity modulated light 34 from a light source 36, e.g., an LED. The AC current is measured by an ammeter 38 and the current's amplitude indicates the surface charge or the electric potential of sample 26.

Figure 2:
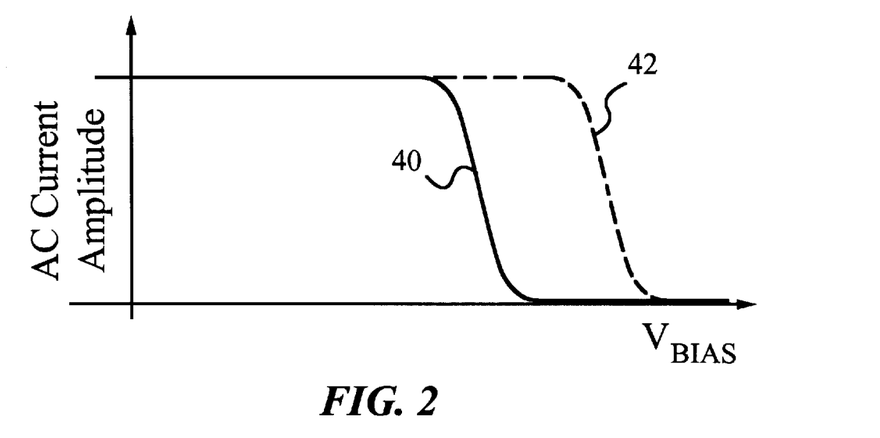
FIG. 2 is a graph of the appropriate bias voltages for deriving surface charge measurements with a LAPS.

It is well-known that $V_{BIAS}$ has to be a reverse bias and it has to be adjusted such that the measurement takes place in the region where the amplitude of the AC current varies and even where it varies most when high resolution measurements are undertaken. In the graph of FIG. 2 curve 40 illustrates the AC current amplitude at a low pH and curve 42 corresponds to high pH. The bias voltage $V_{BIAS}$ is swept and the inflection point is calculated and corresponds to the pH value.

Figure 3A:
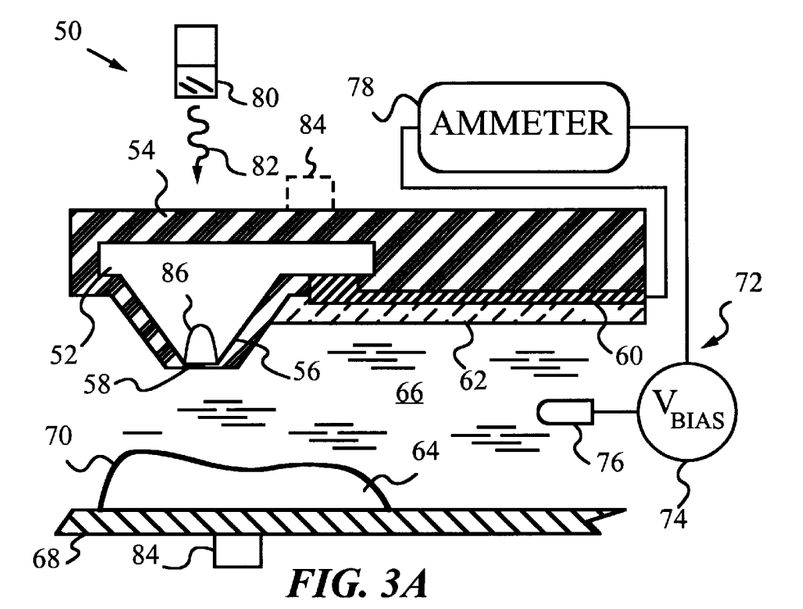
FIG. 3A is a schematic view of a system according to the invention equipped to detect surface charge with an ammeter.

FIG. 3A shows an embodiment of a scanning probe potentiometer or SPP 50 according to the invention. SPP 50 has at its core a semiconductor 52, in this case silicon, covered by an insulator 54. Semiconductor 52 has a shape coming to an apex or tip constituting a probing surface 56. The thickness of insulator 54 covering probing surface 56 is on the order of 100 to 1,000 Angstroms or more. This region of insulator 54 is in fact a charge-sensitive layer 58. The overall shape of SPP 50 can be varied as required for any given application as long as probing surface 56 with charge-sensitive layer 58 protrudes or is otherwise suitably exposed for the purpose of making measurements as described below.

Charge-sensitive layer 58 can be made of the same insulating material as the remainder of insulator 54 or it can have a different composition. Materials such as silicon oxide, oxinitride or nitride or a combination of these materials are preferable.

A metal layer 60 is in contact with semiconductor 52 and provides for an electrical connection to semiconductor 52. A passivation layer 62 covers metal layer 60 to ensure electrical insulation. Passivation layer 62 can be made of the same material as insulator 54 or a different material. For example, both insulator 54 and passivation layer 62 are made up of nitride and oxide layers. A particular method of making SPP 50 indicating the materials selected is discussed below.

A sample 64 is located on a substrate 68 underneath probing surface 56 and is immersed in a conductive medium 66. Sample 64 can consist of DNA, RNA, proteins, receptors, antibodies, bacteria, viruses, polymers, cells, organelles and membranes or any other materials whose potential or charge are to be examined. A surface 70 of sample 64 is exposed for measurement. Depending on the application, medium 66 can by an aqueous electrolytic solution or a gel. For example, medium 66 can be a gel containing a conductor such as KOH. A person of average skill in the art will be able to make the proper choice of medium 66 based on the type of sample 64 and other known factors.

An arrangement 72 is provided for creating a bias voltage $V_{BIAS}$ between sample 64 and semiconductor 52; specifically its probing surface 56. Arrangement 72 has a voltage generator 74 and an electrode 76 immersed in medium 66, which is a part of arrangement 72. Voltage generator 74 is also connected to metal layer 60 via another terminal. It will be understood by a person skilled in the art that numerous variations of arrangement 72 are suitable for generating bias voltage $V_{BIAS}$ as required.

A device 78 for measuring an electrical property of SPP 50 indicating the charge on surface 70 is also connected to metal layer 60. In this embodiment device 78 is an ammeter.

SPP 50 has a light source 80, e.g., a laser or a light emitting diode (LED), for generating light 82. Source 80 is operated such that emerging light 82 is amplitude modulated at a frequency ω. Furthermore, source 80 is positioned and oriented such that light 82 is directed at semiconductor 52 and specifically near probing surface 56.

A scanning mechanism 84 is mounted under substrate 68. Mechanism 84 is designed to move sample 64 with respect to probing surface 56. Preferably, mechanism has three degrees of freedom to accommodate displacement of sample 64 in an x-y plane as well as in the z direction. In the simplest case, mechanism 84 is designed to move sample 64 up and down along the z axis only. Alternatively, substrate 68 can be fixed and the assembly including semiconductor 52 can be driven by mechanism 84 as indicated in dashed lines. Appropriate mechanical designs of mechanism 84 are well-known in the art.

During operation of SPP 50 voltage generator 74 applies bias voltage $V_{BIAS}$ between its electrode 76 and probing surface 56 of semiconductor 52. This causes a depletion region or layer 86 to be created in semiconductor 52 adjacent probing surface 56. When amplitude modulated light 82 from light source 80 penetrates into semiconductor 52 electron-hole pairs are created and diffuse to depletion region 86. An alternating photocurrent is produced when the electron-hole pairs separate in depletion region 86. This AC current is conducted via metal layer 60 and measured by ammeter 78. The amplitude of the AC current indicates the potential or charge of surface 70 of sample 64.

To obtain a complete set of data mechanism 84 scans surface 70 and the measurement is repeated. Although probing surface 56 and specifically charge-sensitive layer 58 is preferably in contact with surface 70 during the measurement process, mechanism 84 can be adjusted to maintain a predetermined distance between them. Provided that tip is positioned within the range of the screening length, the presence of charge on surface 70 can thus be determined in the non-contact mode.

Figure 3B:
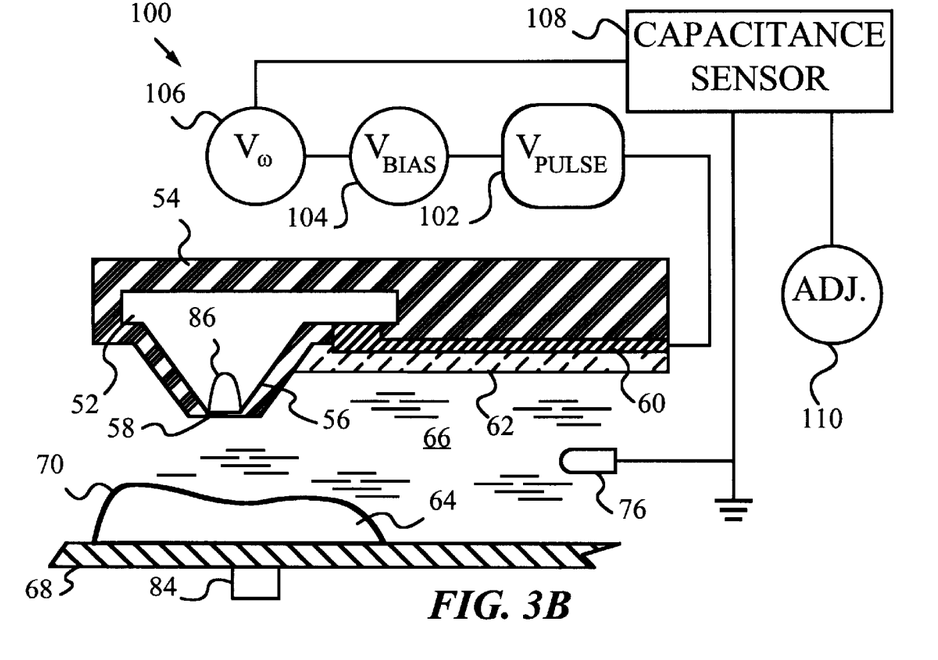
FIG. 3B is a schematic view of a system according to the invention equipped to detect surface charge with a capacitance sensor.

FIG. 3B illustrates another embodiment of an SPP 100 according to the invention. The main difference between SPP 50 of FIG. 3A and SPP 100 resides in the electronic elements and the manner in which the measurement is derived. Consequently, the same parts are labeled with the same reference numerals as in FIG. 3A.

SPP 100 has a pulse generator 102, a bias generator 104 and a modulation voltage generator 106 connected to metal layer 60. Pulse generator 102 is designed to deliver controlled voltage pulses to semiconductor 52 for the purpose of altering surface 70 of sample 64. Bias generator 104 has the same function as voltage generator 74. Modulation voltage generator 106 delivers a voltage signal modulated at frequency ω for the purpose of measuring the derivative of capacitance with respect to voltage.

A capacitance sensor 108 with an adjustment circuit for factoring out background capacitance is also provided. Sensor 108 is designed to measure the capacitance between probing surface and medium 66. To ensure good operation semiconductor 52 and metal layer 60 are well insulated to reduce stray capacitance. This is best accomplished by making insulator 54 and passivation layer 62 thick.

In this embodiment the capacitance is used as the electrical property for measuring the charge on surface 70. Changes in charge accumulated on surface 70 of sample 64 affect the capacitance between semiconductor 52 and medium 66 by altering the width of depletion layer 86. Thus, the operation of SPP 100 is analogous to that of SPP 50 with the exception that capacitance sensor 108 registers the capacitance between probing surface 56 and medium 66.

Both SPP 50 and SPP 100 can be used, e.g., to easily and continuously monitor biochemical reactions down the strand of a DNA oligomer or to measure pH, redox currents, or other charge-related properties. In case of measuring redox currents charge-sensitive layer 58 is preferably a metal and semiconductor 52 is heavily doped. Pulses generated by pulse generator 102 can be used to alter the characteristics of sample 64 during measurement. For example, when sample 64 is a double stranded (ds) DNA sample then the application of such pulses can be used to denature the ds DNA and produce single stranded (ss) DNA. Of course, pulse generator 102 can also be used in SPP 50 when measuring the photocurrent in semiconductor 52.

It will be apparent to a person of average skill in the art that alternative pH-sensitive materials can be used as layer 58 on probing surface 56 to suit the chemical reaction of interest or the particular application. Other materials, such as a layer of gold, may be used on probing surface 56 to measure redox potential of sample 64.

PREFERRED METHOD OF MAKING A SEMICONDUCTOR ASSEMBLY

It is understood that SPP 50 and SPP 100 of the invention can be made by many methods to satisfy the above-mentioned requirements. This preferred method of making the assembly with semiconductor 52 is merely one approach and is not intended as a limitation. The dimensions specified are given for the purposes of illustration only.

FIGS. 4A–K illustrate the individual steps of the method. The process commences in FIG. 4A with a Silicon on Insulator (SOI) wafer 120 having a lightly n doped 10 μm top Si layer 122, a 0.3 μm oxide layer 124 and a thick silicon substrate layer 126. In the second step, shown in FIG. 4B, top Si layer 122 is dry etched to produce a probing tip 128 with an active area or tip 132. Probing tip 128 also has a base 130.

Figure 4A:
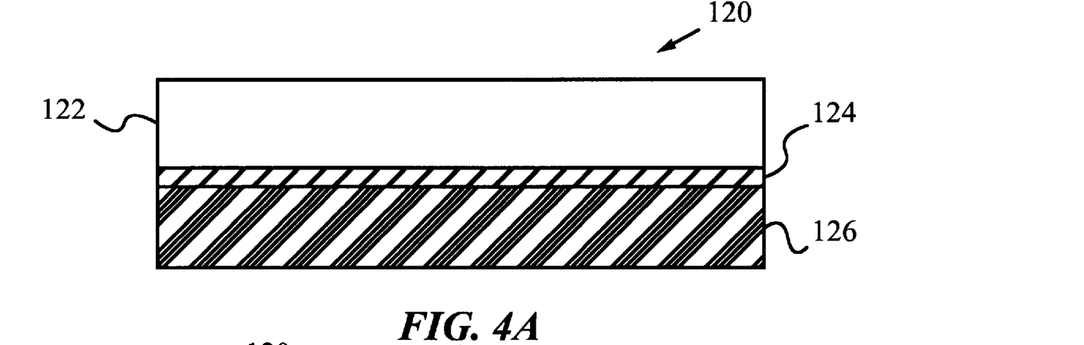
FIG. 4A–4J are cross sectional views illustrating a method of making a scanning probe potentiometer for use in a system according to the invention.
Figure 4B:
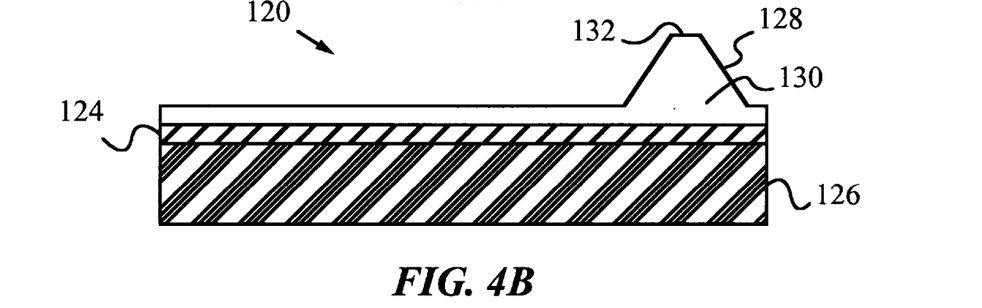
Figure 4C:
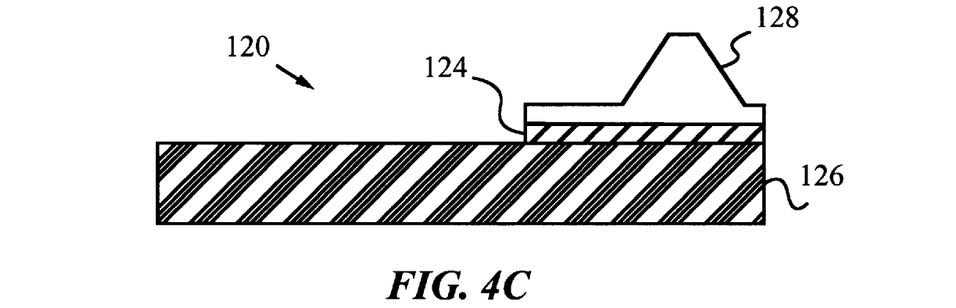
Figure 4D:
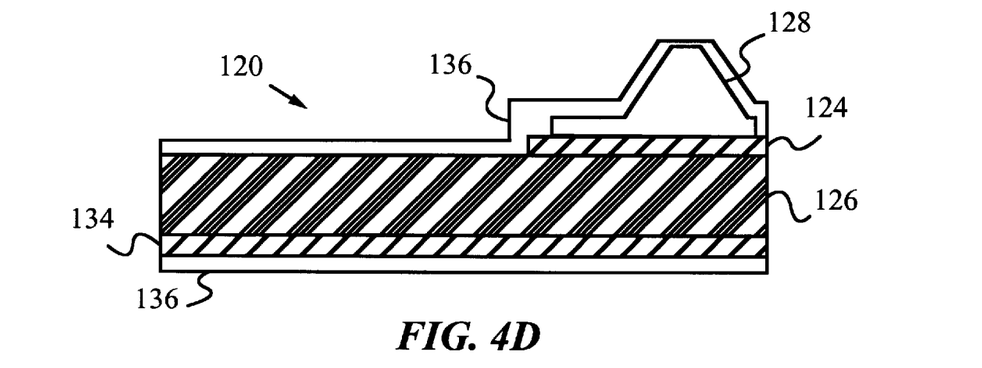
Figure 4E:
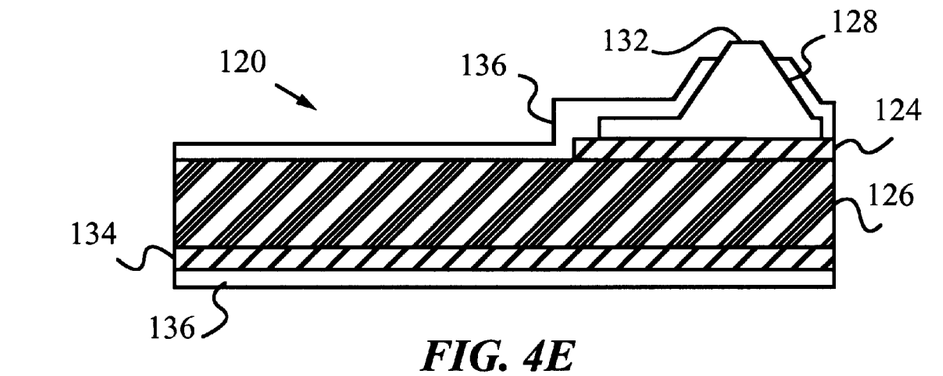

During the third step (see FIG. 4C) an unnecessary portion of Si layer 122 is removed and the portion of oxide layer 124 below that portion is removed as well by etching. After this the bottom of substrate 126 is provided with an oxide layer 134 and a 0.5 μm nitride layer 136 is deposited on SOI wafer 120 without using a mask (see FIG. 4D). Layer 136 is dry etched to the proper thickness. Next, a 1.6 μm layer of photoresist is spun on SOI 120 and photoresist is removed off the active area on tip 132. Nitride layer 136 is dry etched to expose tip 132 of probe tip 128 (see FIG. 4E). The oxide is wet etched to completely strip the active area down to silicon layer 122 before the subsequent regrowing steps.

Figure 4F:
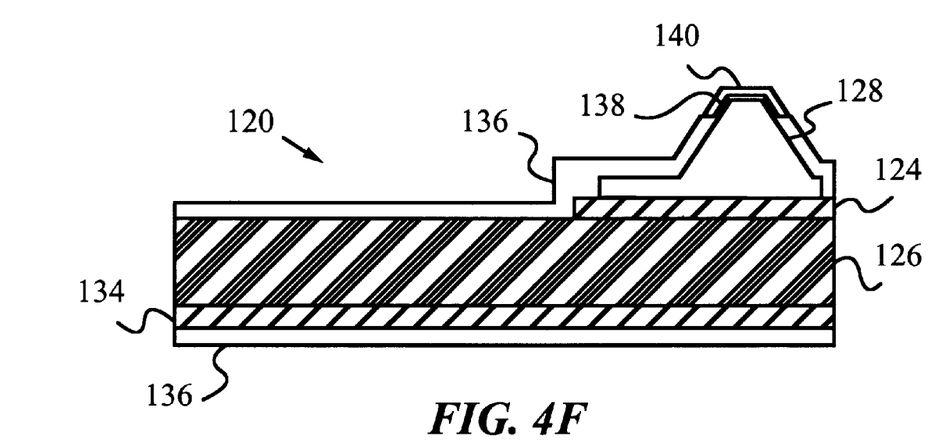
Figure 4G:
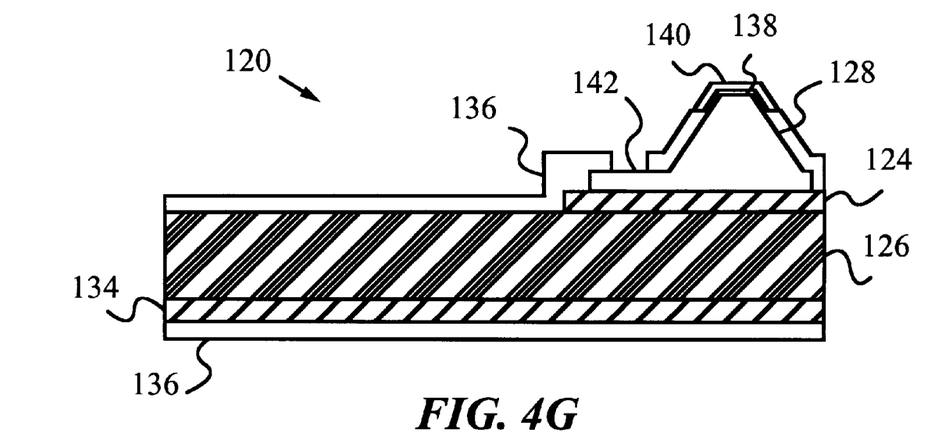

During the next step a 300 Angstrom thick thermal oxide layer 138 is formed on exposed tip 132. Then an 800 Angstrom nitride layer 140 is deposited on thermal oxide layer 138 (see FIG. 4F). Now, a thick layer of photoresist is spun on to cover entire SOI wafer 120 and leave exposed a region over silicon layer 122. Then the nitride is dry etched and the oxide is wet etched such that a contact hole 142 is produced where nitride layer 136 was exposed (see FIG. 4G). This step is also used to define a nitride cantilever structure described below.

Figure 4H:
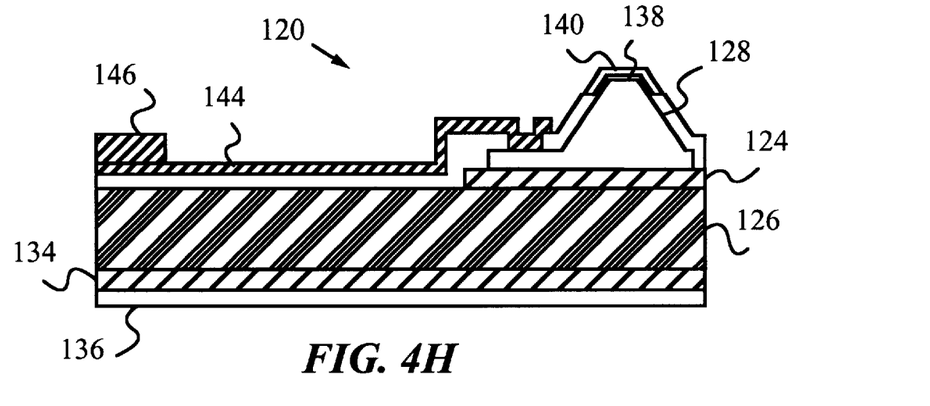

In the next step a metal layer 144, e.g., Al, is evaporated on top of nitride layer 136 such that some Al enters into contact hole 142. This is important to ensure good electrical contact between metal layer 144 and probing tip 128. A thick photoresist is then spun on SOI 120 and metal layer 144 is wet etched to proper dimensions. A metal pad 146 is evaporated on metal layer 144 while a thick photoresist layer protects SOI 120. The photoresist is removed once pad 146 is properly formed (see FIG. 4H).

Figure 4I:
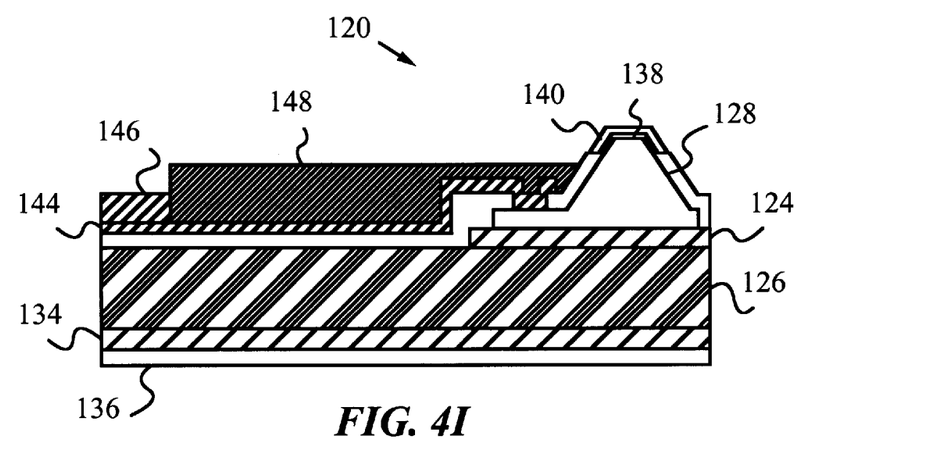

During the following step a passivation layer 148 is deposited on top of metal layer 144 and around probing tip 128 while keeping active area or tip 132 exposed. The thickness of passivation layer 148 is approximately 0.5 μm and thus sufficient to ensure proper insulation of metal layer (see FIG. 4I). Passivation layer 148 can be nitride deposited by PECVD and/or low-temperature-oxide (LTO). Nitride requires dry etching and low-temperature-oxide requires wet etching at the end of the present method. LTO beneath the nitride is preferred since it is most effective in protecting active area from plasma etches during the remainder of the process.

Figure 4J:
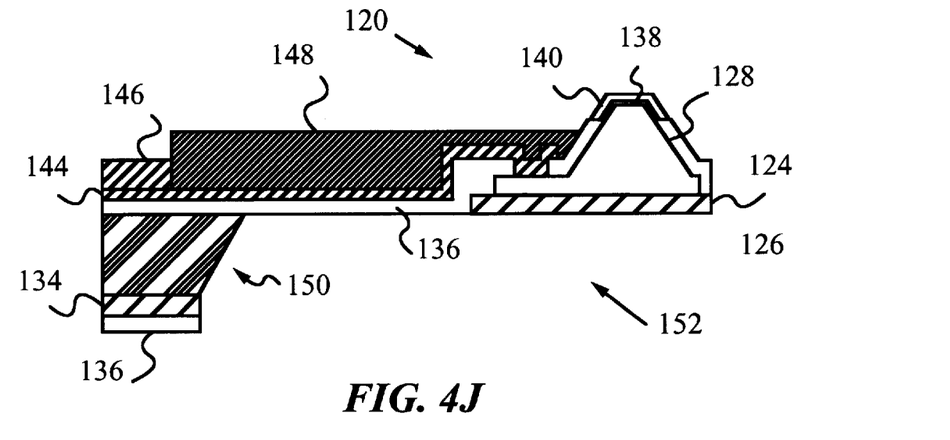

Finally, during the last step, bottom nitride layer 136, oxide layer 134 and substrate silicon layer 126 are removed by etching with the exception of a mechanical support block 150. A polyimide mask is used on the top of SOI 120 and on the surface of block 150 to perform this step. Then the mask is removed to yield a finished semiconductor assembly 152, as illustrated in FIG. 4J. Tip 132 of assembly 152 is the probing surface while thermal oxide layer 138 together with nitride layer 140 constitute the charge-sensitive layer.

Figure 5:
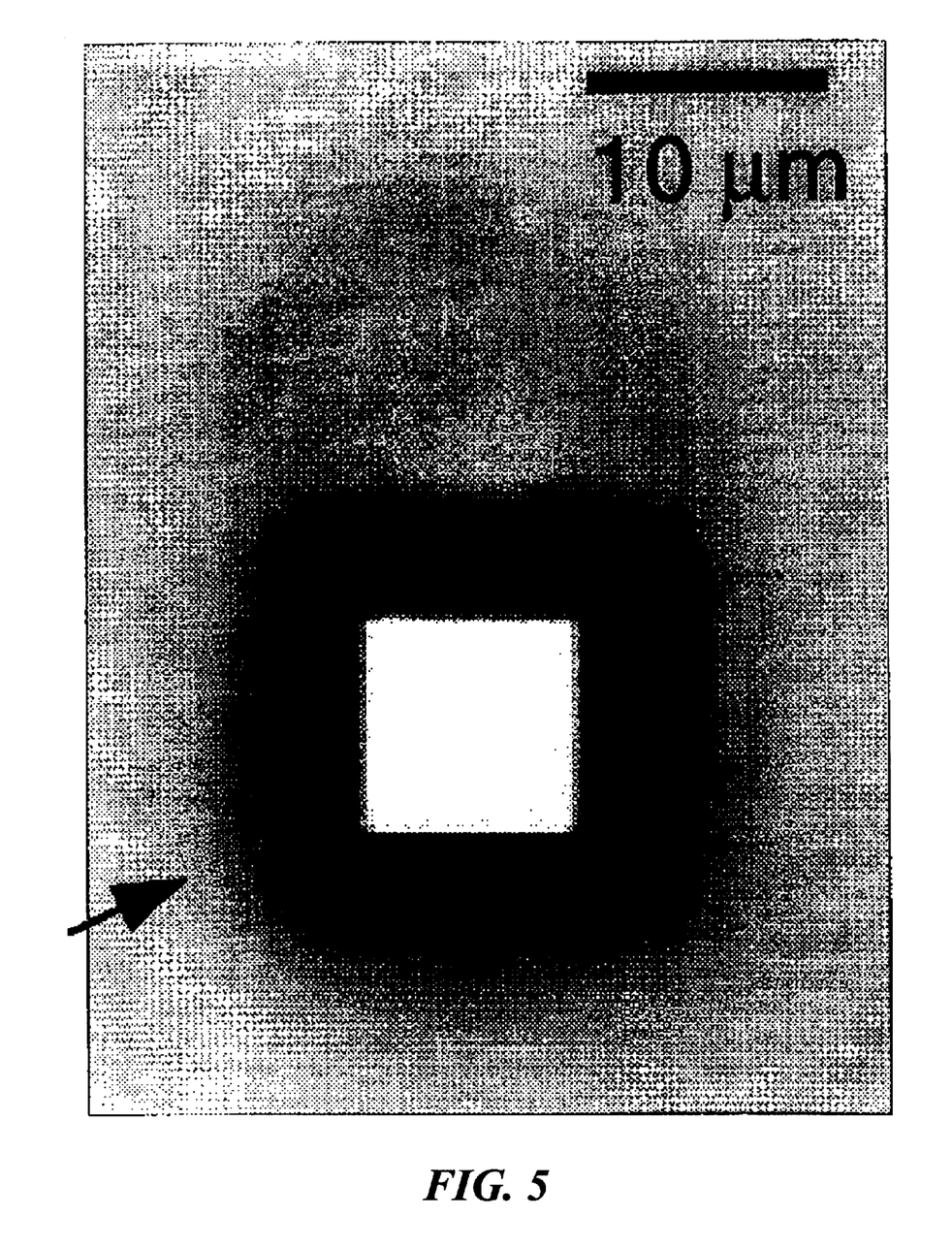
FIG. 5 is a microscope image of a probing tip of a scanning probe potentiometer according to the invention.

FIG. 5 shows a microscope image of tip 132 of assembly 152 as seen from the top. The probing surface is square with approximate dimensions of 10 by 10 μm. The preferred method can be used to produce even smaller tips, e.g., less than 1 μm$^2$ or larger ones having a surface area of 100 μm$^2$ or more. The actual dimensions required will be determined by a person skilled in the art based on the practical considerations.

PREFERRED EMBODIMENT

Figure 6:
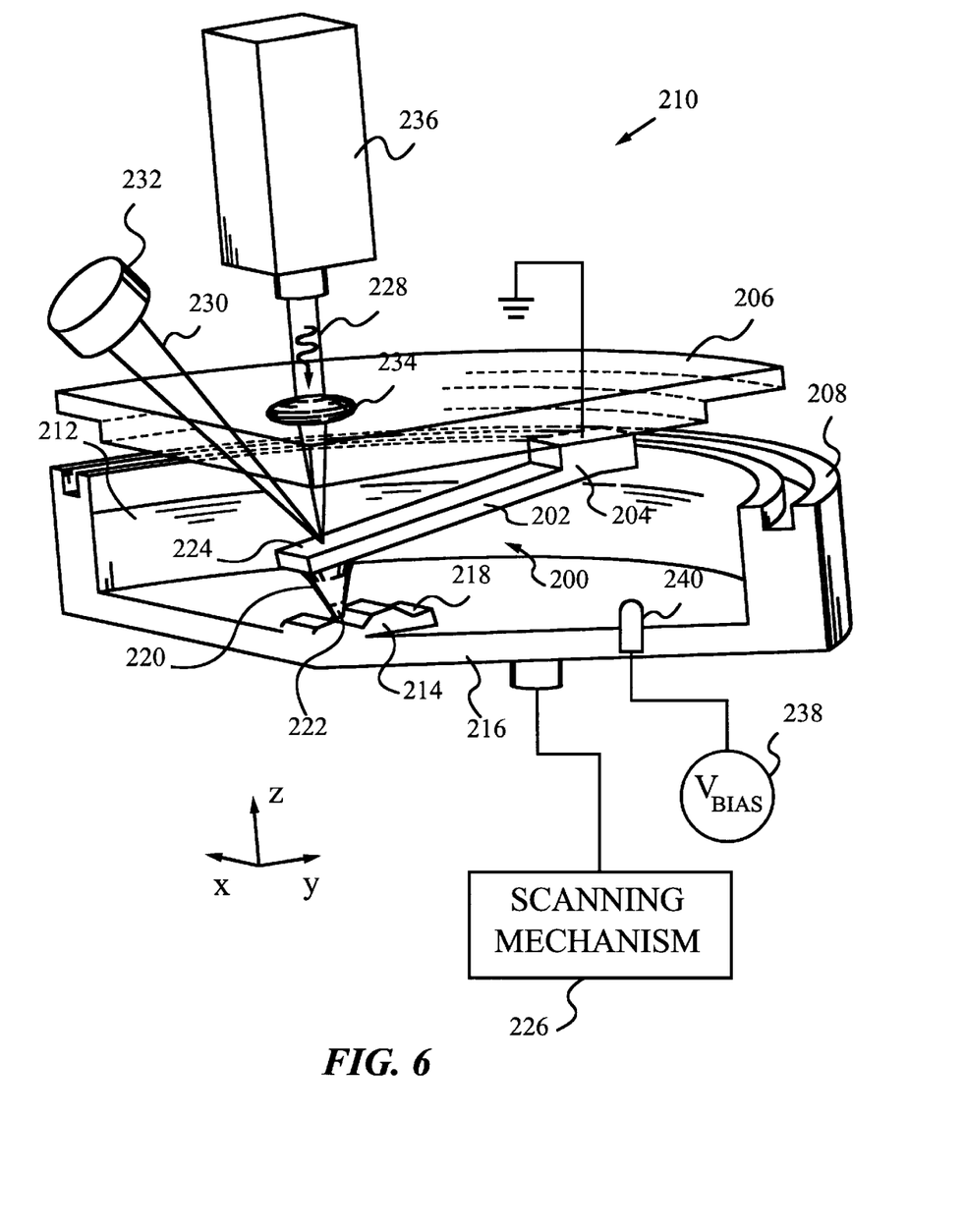
FIG. 6 is a three dimensional view of a preferred system according to the invention employing a scanning probe potentiometer in the form of a cantilever.

In a preferred embodiment of the invention a system 210 has an SPP 200 consisting of a semiconductor assembly 202 produced according to the preferred method. FIG. 6 shows a three dimensional cut out of system 210. Semiconductor assembly 202 is a cantilever structure mounted by a block 204 (analogous to block 150) on the underside of a lid structure or cover 206. Cover 206 is made of a material transparent to light at the wavelength used in measurement.

A reservoir or vessel 208 designed to be sealed by cover 206 in a liquid-tight manner contains a medium 212, preferably an electrolytic solution. The side wall of vessel 208 has a groove for receiving a sealing ring (not show) to ensure impermeability. A sample 214 is disposed on a bottom 216 of vessel 208. A surface 218 of sample 214 is exposed for scanning.

Cantilever 202 has a probing tip 220 disposed above sample 214. Probing tip 220 tapers down to an apex or tip 222 which is covered with thermal oxide and nitride as described above. A top surface 224 of cantilever 202 is flat.

A scanning mechanism 226 is attached to vessel 208 and allows to move sample 214 with respect to probing tip 220 in the x, y and z directions.

A laser 236 emits a light beam 228 which is amplitude modulated at a frequency 107. The mechanism required to perform the amplitude modulation is well known in the art and can be based on the principles of Q-switching, acousto-optic modulation or electro-optic modulation. Light beam 228 is focused by a focusing optic 234, e.g., a focusing lens, on surface 224 of cantilever 202. The wavelength of beam 228 is chosen such that it is suitable for creating electron-hole pairs in the depletion layer within the semiconductor. Another portion of beam 228 is reflected from surface 224 in a reflected beam 230.

A deflection sensor 232 is located in the path of reflected beam 230 to measure the deflection of cantilever 202. This type of deflection measuring system for cantilevers is well-known in the art.

A voltage source 238 with an electrode 240 immersed in electrolyte 212 is provided for producing bias voltage $V_{BIAS}$. An additional reference electrode (not shown) may also be placed in electrolyte 212 to monitor bias voltage $V_{BIAS}$.

The scanning of sample 214 is performed by moving tip 222 over surface 218 and the surface charge or potentiometric measurements are obtained as described above. Additionally, the topology of surface 218 is also determined by cantilever 202 by measuring the deflection of reflected beam 230 with the aid of sensor 232. Thus, both the topology and surface charge of sample 214 are obtained in one scanning cycle.

System 210 provides—a new form of scanning probe charge detection in which the surface charges are detected by measuring the electrical properties of tip 222 rather than the deflection of cantilever 202 due to electrostatic forces. This allows for a direct measure of the surface charge that is not influenced by factors such as topography and other undesirable surface/tip interactions. Measurements of pH changes are accessible on the molecular level, i.e., a chemical reaction on a selected molecule may be monitored. In addition, the charge distribution of a surface of a sample may be mapped without regard to its topography.

Of course, the preferred embodiment can also be modified to perform its charge measurements based on capacitance rather than the alternating photocurrent. In this case the deflection measuring system for cantilever 202 does not generate light beam 228 at the wavelength required to produce electron-hole pairs in the semiconductor. Alternatively, the deflection measuring system in this situation can be replaced by one which does not use any light beams at all (e.g., a piezoelectric deflection measuring device).

In essence, the preferred embodiment integrates the selective charge measurement system of LAPS with a force-sensitive cantilever system similar to an atomic force microscope (AFM). In embodiments in which it is desired to scan large surface areas, multiple tips are fabricated onto the same cantilever. For example, integrated LAPS and AFM system 210 can be modified to include 5 tips. In particular, when using 5 tips with a 200 μm pitch and scanning at a frequency of approximately 50 Hz the charge density on a 1 mm$^2$ surface can be mapped in roughly 20 seconds with a lateral resolution of 0.2 μm.

Figure 7A:
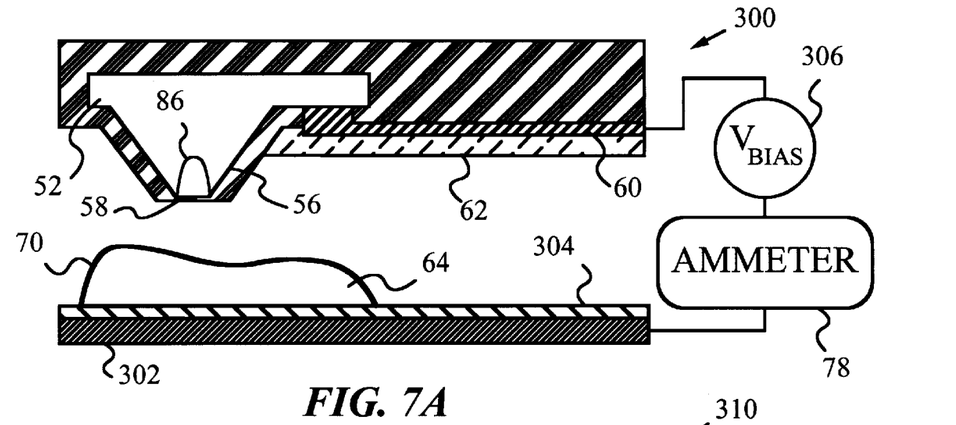
FIG. 7A–7B are schematic views showing embodiments in which the sample is positioned on a conducting plate.
Figure 7B:
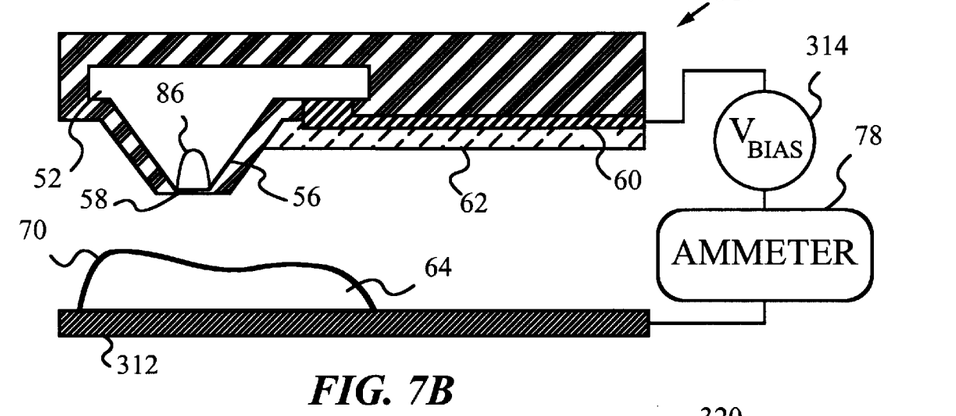

FIGS. 7A–B illustrate two alternative embodiments of the invention similar to the systems shown in FIGS. 3A–B but requiring no medium. The same reference numbers are used for the same parts. FIG. 7A shows an SPP system 300 in which sample 64 is positioned on a conducting plane in the form of a metal plate 302 covered with an insulator 304. For precise measurements insulator 304 should be kept thin. A voltage generator 306 is connected to conducting plate 302 and to metal layer 60 for applying the required bias voltage $V_{BIAS}$ between semiconductor 52 and conducting plate 302.

FIG. 7B shows a SPP system 310 in which sample 64 is positioned directly on a metal plate 312. Again, a voltage generator 314 is used to establish bias voltage $V_{BIAS}$ between semiconductor 52 and plate 312.

Figure 8:
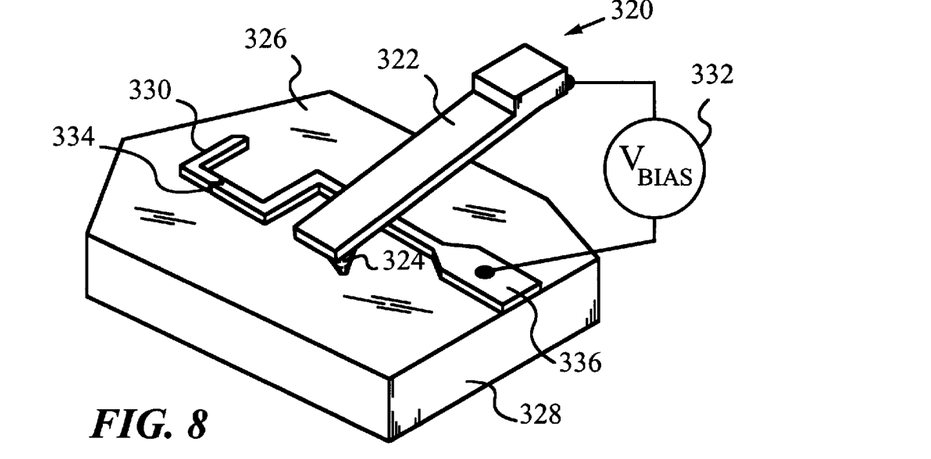
FIG. 8 is an isometric view illustrating another alternative embodiment of the invention.

Finally, FIG. 8 shows an embodiment of an SPP system 320 using a cantilever structure 322 with a probing tip 324 for scanning a surface 326 of a substrate 328. A sample 330 is a conductive trace deposited on surface 326. A voltage generator 332 is connected between a pad 336 of trace 330 and cantilever 322 for applying the requisite bias voltage $V_{BIAS}$. This embodiment is particularly useful in examining an electronic circuits. That is because breaks and discontinuities in the circuit can be easily monitored. For example, a break 334 in trace 330 will register via a difference in surface potential of trace 330 on either side of break 334.

Based on the above description, one skilled in the art will appreciate that many alternative embodiments exist possible embodiments that would apply to this invention. In particular, the various embodiments of the SPP system can be used in many fields for performing accurate surface charge or potential measurements and mapping out the surface topography at the same time, if required. Therefore, the scope of the invention should be construed in light of the appended claims.

What is claimed is:

1. A system for measuring a surface charge of a sample by scanning said sample, said system comprising:
   (a) a semiconductor having a probing surface;
   (b) a charge-sensitive layer disposed on said probing surface;
   (c) a means for creating a bias voltage $V_{BIAS}$ between said sample and said semiconductor to produce a depletion layer in said semiconductor;
   (d) a means for measuring an electrical property of said system, said electrical property indicating said surface charge; and
   (e) a scanning means for moving said sample relative to said probing surface.

2. The system of claim 1 wherein said means for creating said bias voltage $V_{BIAS}$ comprise a conductive medium in which said semiconductor and sample are immersed.

3. The system of claim 2 wherein said conductive medium is an aqueous electrolytic solution.

4. The system of claim 2 wherein said conductive medium is a gel.

5. The system of claim 1 wherein said means for creating said bias voltage $V_{BIAS}$ comprise a conducting plane and said sample is positioned on said conducting plane.

6. The system of claim 5 wherein said conducting plane is covered by an insulator and said sample is positioned on said insulator.

7. The system of claim 1 wherein said semiconductor comprises a cantilever having a probing tip and said probing surface is located on said probing tip.

8. The system of claim 7 further comprising a laser deflection system generating a light beam for measuring a deflection of said cantilever.

9. The system of claim 8 wherein said light beam has an amplitude modulated frequency ω for penetrating into said semiconductor and creating electron-hole pairs in said semiconductor.

10. The system of claim 7 further comprising a cantilever deflection measuring system for measuring the topology of said sample.

11. The system of claim 1 wherein said means for measuring said electrical property is an ammeter and said electrical property is an alternating current in said semiconductor.

12. The system of claim 1 wherein said means for measuring said electrical property is a capacitance meter and said electrical property is a capacitance.

13. The system of claim 12 wherein said means for creating said bias voltage $V_{BIAS}$ comprise a medium in which said semiconductor and said sample are immersed and said capacitance exists between said medium and said semiconductor.

14. The system of claim 12 wherein said means for creating said bias voltage $V_{BIAS}$ comprise a conductive plane on which said sample is positioned and said capacitance exists between said conductive plane and said semiconductor.

15. The system of claim 1 wherein said sample consists of a material selected from the group consisting of DNA, RNA, proteins, receptors, antibodies, bacteria, viruses, polymers, cells, organelles and membranes.

16. The system of claim 1 wherein said charge-sensitive layer is selected from the group of materials consisting of pH sensitive materials, semiconducting materials and metals.

17. A method of measuring a surface charge of a sample by scanning said sample, said method comprising the steps of:
   (a) providing a semiconductor having a probing surface;
   (b) disposing a probing layer on said probing surface;
   (c) generating a bias voltage $V_{BIAS}$ to create a depletion layer in said semiconductor;
   (d) scanning said sample with said probing surface; and
   (e) measuring an electrical property of said system, said electrical property indicating said surface charge of said sample.

18. The method of claim 17 further comprising the step of immersing said semiconductor and said sample in a conductive medium for applying said bias voltage $V_{BIAS}$.

19. The method of claim 18 wherein said conductive medium is an aqueous electrolytic solution.

20. The method of claim 18 wherein said conductive medium is a gel.

21. The method of claim 17 further comprising the step of placing said sample on a conducting plane and applying said bias voltage $V_{BIAS}$ between said conducting plane and said semiconductor.

22. The method of claim 17 wherein said semiconductor forms a portion of a cantilever and said method further comprises the steps of providing said cantilever with a probing tip and disposing said probing surface on said probing tip.

23. The method of claim 22 further comprising the step of measuring a deflection of said cantilever using a light beam.

24. The method of claim 23 wherein said light beam has an amplitude modulated frequency $\omega$ for penetrating into said semiconductor and creating electron-hole pairs in said depletion layer.

25. The method of claim 22 further comprising the step of measuring the deflection of said cantilever to determine the topology of said sample.

* * * * *